US005723654A

United States Patent [19]
Bertsch

[11] Patent Number: 5,723,654
[45] Date of Patent: Mar. 3, 1998

[54] PROCESS FOR THE PREPARATION OF ALKYL 2-FLUORO-ISOBUTYRATES

[75] Inventor: Achim Bertsch, Köln, Germany

[73] Assignee: Bayer Aktiengesellschaft, Leverkusen, Germany

[21] Appl. No.: 668,493

[22] Filed: Jun. 17, 1996

[30] Foreign Application Priority Data

Jun. 22, 1995 [DE] Germany ............ 195 22 703.4

[51] Int. Cl.[6] .................................................. C07C 69/63
[52] U.S. Cl. ................................................ 560/227
[58] Field of Search ................................. 560/227

[56] References Cited

FOREIGN PATENT DOCUMENTS

| 0468681 | 1/1992 | European Pat. Off. . |
| 0506059 | 9/1992 | European Pat. Off. . |
| 0509544 | 10/1992 | European Pat. Off. . |
| 0645365 | 3/1995 | European Pat. Off. . |
| 4131242 | 4/1993 | Germany . |
| 08127555 | 5/1996 | Japan . |
| 9424086 | 10/1994 | WIPO . |

OTHER PUBLICATIONS

E. Fritz-Langhals, "Alkali Metal . . . Benzenes", Tetrahedron: Asymmetry, vol. 5, No. 6, pp. 981–986, 1994.
W.J. Gensler, et al., Fluorination of Methyl Isobutyrate with Perchloryl Fluoride[1], J. Org. Chem., vol. 33, No. 11, pp. 4279–4281, (1968).
E. Fritz-Langhals, Alkali Metal Fluorides as Efficient Fluorinating Agents, Enantiocontrolled Synthesis of 2-Fluoroalkyl Carboxylates and 1-Fluoroalkyl Benzenes, Tetrahedron: Asymmetry, vol. 5, No. 6, pp. 981–986, (1994).

*Primary Examiner*—Gary Geist
*Assistant Examiner*—Rosalynd Keys
*Attorney, Agent, or Firm*—Sprung Kramer Schaefer & Briscoe

[57] ABSTRACT

Alkyl 2-fluoro-isobutyrates are prepared by reacting the corresponding sulphonic esters with potassium fluoride in an acid amide as solvent and in the presence of a base.

7 Claims, No Drawings

PROCESS FOR THE PREPARATION OF ALKYL 2-FLUORO-ISOBUTYRATES

The present invention relates to a process for the preparation of alkyl 2-fluoro-isobutyrates, which are important intermediates for the preparation of fungicides and herbicides (see, e.g., EP-A1 0 381 330 and WP 90/09378).

A number of laboratory syntheses for 2-fluoro-isobutyric esters are described in the literature, which all have considerable disadvantages, however, if they are to be converted to the industrial scale.

2-Fluoro-isobutyric esters can be obtained, for example, from 2-bromo-isobutyric esters by halogen exchange with silver fluoride at 140° C. (see J. Org. Chem. 33 4279 (1968)). Disadvantages in this case are the low selectivity of only 20% and the high cost of silver fluoride.

EP-A1 0 509 544 describes an analogous reaction with potassium fluoride in 2,3-butanediol at 120° C. The maximum yield, only determined by gas chromatography, is 45%. The predominant formation of methacrylic esters by an elimination reaction is an interference.

The addition of hydrogen fluoride to methyl methacrylate is also described in EP-A1 0 509 544. The maximum yield is only 25%. Disadvantages of this process, which, although it starts from inexpensive starting materials, are, in addition to the low yield, the use of toxic and corrosive hydrogen fluoride/pyridine mixtures which are complex to work up, and the employment of reaction temperatures, at which autoclaves made of corrosion-resistant materials must be used. If the reaction is carried out in anhydrous hydrogen fluoride which permits simple recovery, the yield falls to only 16%.

EP-A1 0 506 059 describes the synthesis of 2-fluoro-isobutyric esters starting from 2-hydroxy-isobutyric esters by reaction with fluoro- or chlorosulphonic acid and hydrogen fluoride or hydrogen fluoride/pyridine mixtures. A disadvantage in this case is the work-up of the of waste water containing large amounts of hydrogen fluoride and possibly pyridine. In addition, the formation of considerable amounts of methacrylic esters is again an interference, which is declared by the applicant himself in the later application WO 94/24086.

In EP-A1 0 468 681, the direct exchange of the hydroxyl group for fluorine in 2-hydroxy-2,2dialkylacetates is described with sulphur tetrafluoride or diethylaminosulphur trifluoride as reagent. The outstanding yields are opposed here by the use of sulphur tetrafluoride which is toxic and not available in industrial amounts.

In WO 94/24086, the preparation of 2-fluoro-isobutyric esters from 2-hydroxy-isobutyric esters in a two-stage process by reaction with thionyl chloride, followed by reaction with hydrogen fluoride or hydrogen fluoride/amine mixtures is described. Again, a disadvantage is the use of hydrogen fluoride, in particular in a mixture with amines. Furthermore, the hydrogen-chloride-containing hydrogen fluoride produced here requires very expensive special materials in order to be able to carry out the aqueous work-up.

In Tetrahedron Asymmetry 5, 981 (1994), the fluorination of 2-alkyl-2-sulphonyloxy acetic esters which are 2-substituted with hydrogen, i.e. secondary, is described. Retention of enantiomeric purity when chiral starting materials are used, e.g. (S)-lactic esters is evidence here of the course of the reaction with reverse of configuration via an $S_N2$ mechanism.

A process has now been found for the preparation of alkyl 2-fluoro-isobutyrates of the formula (I),

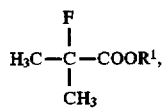

in which

R$^1$ denotes an unbranched or branched and/or unfluorinated or fluorinated alkyl radical having 1 to 4 carbon atoms, which is characterized in that a sulphonic ester of the formula (II)

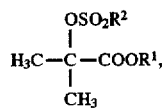

in which

R$^1$ has the meaning given under formula (I) and

R$^2$ independently of R$^1$, has the same scope of meanings as R$^1$, is reacted with potassium fluoride in a solvent of the formula (III)

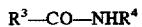

in which

R$^3$ and R$^4$, independently of each other, each denote hydrogen, phenyl or alkyl having 1 to 4 carbon atoms.

Examples of these radicals R$^1$ and R$^2$ are methyl, trifluoromethyl, ethyl, n-propyl, i-propyl, n-butyl, i-butyl and tert-butyl. Preference is given to methyl and ethyl. Particularly preferably, methyl 2-methanesulphonyloxy-isobutyrate is used, and methyl 2-fluoro-isobutyrate is prepared therefrom.

Sulphonic esters of the formula (II) can be readily prepared in a manner known per se, e.g. from the corresponding 2-hydroxy-isobutyric esters by reaction with acid chlorides or acid anhydrides which comprise the radical R$^2$ and a chlorosulphonic anhydride group or a sulphonic anhydride group. This reaction is preferably carried out in the presence of bases. Bases which can be used are, e.g., organic bases such as tertiary amines or inorganic bases such as sodium bicarbonate.

The potassium fluoride can be used in a commercial form. Preferably, it is finely powdered.

The sulphonic esters of the formula (II) are preferably admixed with an excess of potassium fluoride. Suitable amounts are, e.g., 1.05 to 20 mol, in particular 2 to 5 mol of potassium fluoride per mol of sulphonic ester of the formula (II).

Preferred solvents of the formula (III) are those in which R$^3$ and R$^4$, independently of each other, each denote hydrogen or methyl. Particular preference is given to formamide. Mixtures of solvents of the formula (III) and other solvents can also be used, such mixtures preferably containing at least 20% by weight of one or more of the solvents of the formula (III). It is not absolutely necessary that all of the reaction components must dissolve completely in the solvent or in the solvent mixture. The solvents can be used, e.g., at 2 to 5 times the amount by weight, based on sulphonic ester of the formula (II).

The reaction temperature can be, e.g., in the range 40° to 140° C. Preferably, the temperature is 50° to 110° C., particularly preferably 55° to 90° C.

The reaction times can be, e.g., between 30 minutes and 15 hours.

In a preferred procedure, the potassium fluoride and the solvent (mixture) are introduced. Then, in the course of 5 to 200 minutes, a sulphonic ester of the formula (II) with $R^1$ and $R^2$=unfluorinated or fluorinated $C_1$-$C_2$-alkyl is added dropwise and the alkyl 2-fluoro-isobutyrate is continuously distilled off from the reaction mixture at reduced pressure.

If the alkyl 2-fluoro-isobutyrate isolated after carrying out the process of the invention contains interfering methacrylic ester, this can be trapped, if necessary, by addition of chlorine or bromine. In this case, a procedure can be carried out, for example, in such a manner that titration is formed with bromine until the methacrylic ester has reacted to completion, then the mixture is decolorized by washing with a sparing amount of sodium bisulphite solution and highly pure alkyl 2-fluoro-isobutyrate is obtained in a subsequent vacuum distillation.

The process of the invention permits alkyl 2-fluoro-isobutyrates to be prepared in good yields under mild conditions with readily accessible starting products and reagents. The disadvantages described at the outset with the processes of the prior art do not occur or occur to a very minor extent. In particular, it is not necessary to use starting materials and reagents which are not readily available, are toxic and expensive, and it is not necessary to use particularly corrosion-resistant materials for the reaction and work-up of the reaction mixture.

It is extremely surprising that the fluorination reaction of the invention can also be performed in good yields on the tertiary C atom of sulphonic esters of the formula (II), since an $S_N2$ mechanism is not possible in this case. The reaction of the invention must proceed via a substantially monomolecular carbenium-ion-like transition state. Despite this, the elimination to form methacrylates, against expectation, is only a side reaction.

EXAMPLES

Example 1 a) Methyl 2-methanesulphonyloxy-2-methylpropionate.

A solution of 550 g of methanesulphonyl chloride in 400 ml of tert-butyl methyl ether (MTBE) was added dropwise with cooling at a maximum of 25° C. to a solution, prepared with exclusion of moisture, of 473 g of methyl 2-methyllactate and 607 g of triethylamine in 1200 ml of MTBE. The mixture was then slowly heated to 60° C. and further stirred for 1 hour at this temperature. The reaction mixture was then poured into 1.6 kg of ice water, the phases forming were separated and the water phase was extracted three times with a total of 1200 ml of MTBE. The combined organic phases were washed twice with a total of 1600 ml of 10% strength by weight hydrochloric acid and once each with aqueous sodium hydrogen carbonate solution and sodium chloride solution. After drying over magnesium sulphate, the mixture was concentrated at a maximum of 30° C. on a rotary evaporator and then further dried with stirring in high vacuum. The yield was 616 g(=80.1% of theory). The product had a purity of 94% (GC).

b) Methyl 2-fluoro-isobutyrate 93 g of anhydrous potassium fluoride were dissolved in 220 ml of dry formamide at 60° C. in a 500 ml flask having a mechanical stirrer, internal thermometer, dropping funnel and distillation attachment. The pressure was decreased to 15 mbar and then 78.5 g of the sulphonic ester prepared according to a) were added dropwise in the course of 3 hours. The product formed distilled over. After addition of the sulphonic ester was completed, the mixture was allowed to react for a further 3 hours. The yield was 31.4 g of distillate, which contained, according to GC, 75% by weight of methyl 2-fluoro-isobutyrate, 17% by weight of methyl methacrylate, 0.5% by weight of formamide and low-boilers of unknown composition. The relative yield of desired product was 50% of theory.

Example 2

A procedure analogous to Example 1b) was employed, and 186 g of potassium fluoride were introduced in 440 ml of formamide and reacted with 157 g of the sulphonic ester. 67.7 g of crude product of the same composition as Example 1b) were obtained. 18 g of bromine were then added dropwise to the crude product with ice cooling and then the mixture was decolorized by washing with 15 ml of aqueous sodium bisulphite solution. The mixture was then distilled at 100 mbar via a 10 cm Vigreux column. After 4.3 g of first runnings (77% by weight of desired product), 44.6 g(=46% of theory) of 99% by weight methyl 2-fluoro-isobutyrate distilled over at 51° to 53° C. A further 2.7 g of 89% by weight product were obtained as last runnings. The total yield of the desired compounds was therefore 52% of theory.

Example 3

The procedure was followed as in Example 2, but the sulphonic ester was added dropwise at 90° C. in the course of 1 hour. In this manner, 56.7 g of crude product of the composition 74% by weight of methyl 2-fluoro-isobutyrate, 21% by weight of methyl methacrylate and 2.7% by weight of formamide were obtained. The relative yield of the desired compound was 44% of theory.

What is claimed is:

1. A process for the preparation of an alkyl 2-fluoro-isobutyrate of the formula (I)

in which $R^1$ denotes an unbranched or branched, unfluorinated or fluorinated alkyl radical having 1 to 4 carbon atoms, in which a sulfonic ester of the formula (II)

in which $R^1$ has the meaning given under formula (I) and $R^2$ independently of $R^1$, has the same scope of meanings as $R^1$, is reacted with potassium fluoride in a solvent of the formula (III)

in which $R^3$ and $R^4$, independently of each other, each denote hydrogen, phenyl or alkyl having 1 to 4 carbon atoms.

2. The process of claim 1, in which $R^1$ and $R^2$, independently of each other, represent methyl, trifluoromethyl, ethyl, n-propyl, i-propyl, n-butyl, i-butyl or tert-butyl and $R^3$ and $R^4$, independently of each other, represent hydrogen or methyl.

3. The process of claim 1, in which the sulfonic ester of the formula (II) used is methyl 2-methanesulfonyloxyisobutyrate and the alkyl 2-fluoro-isobutyrate prepared therefrom is methyl 2-fluoro-isobutyrate.

4. The process of claim 1, in which the solvent used is formamide.

5. The process of claim 1, in which, based on 1 mol of sulfonic ester of the formula (II), 1.05 to 20 mol of potassium fluoride and 2 to 5 times the amount by weight of solvent are used.

6. The process of claim 1, in which the reaction temperature is in the range 40° to 140° C.

7. The process of claim 1, in which the alkyl 2-fluoro-isobutyrate formed is removed from the reaction mixture by distillation.

* * * * *